(12) United States Patent
Shor et al.

(10) Patent No.: US 10,101,312 B2
(45) Date of Patent: Oct. 16, 2018

(54) METHODS AND SYSTEMS TO REPLICATE SOIL PROPERTIES

(71) Applicant: University of Connecticut, Farmington, CT (US)

(72) Inventors: Leslie M. Shor, Coventry, CT (US); Jessica Furrer Chau, Columbia, SC (US); Daniel J. Gage, Columbia, CT (US)

(73) Assignee: University of Connecticut, Farmington, CT (US)

( * ) Notice: Subject to any disclaimer, the term of this patent is extended or adjusted under 35 U.S.C. 154(b) by 0 days.

(21) Appl. No.: 14/957,140

(22) Filed: Dec. 2, 2015

(65) Prior Publication Data

US 2016/0153954 A1    Jun. 2, 2016

Related U.S. Application Data

(60) Provisional application No. 62/086,485, filed on Dec. 2, 2014.

(51) Int. Cl.
   *G01N 33/24*    (2006.01)

(52) U.S. Cl.
   CPC ..... *G01N 33/246* (2013.01); *G01N 2033/245* (2013.01)

(58) Field of Classification Search
   CPC .................. G01N 33/246; G01N 2033/245
   USPC .......................................................... 435/29
   See application file for complete search history.

(56) References Cited

U.S. PATENT DOCUMENTS

| | | | | |
|---|---|---|---|---|
| 2002/0061584 A1* | 5/2002 | Farone | ...................... | B09C 1/10 |
| | | | | 435/262.5 |
| 2002/0123546 A1* | 9/2002 | Bigg | ...................... | A61L 15/26 |
| | | | | 524/306 |
| 2004/0072278 A1* | 4/2004 | Chou | ...................... | G01N 35/00 |
| | | | | 435/29 |

OTHER PUBLICATIONS

Addae-Mensah, K.A., Retterer, S., Opalenik, S.R., Thomas, D., Lavrik, N.V., Wikswo, J.P., 2009. Cryogenic Etching of Silicon: An Alternative Method for Fabrication of Vertical Microcantilever Master Molds. J Microelectromech Syst 19.

Chau, J.F., Bagtzoglou, A.C., Willig, M.R., 2011. The effect of soil texture on richness and diversity of bacterial communities. Environmental Forensics 12, 333-341.

Chau, J.F., Or, D., 2006. Linking drainage front morphology with gaseous diffusion in unsaturated porous media: A lattice Boltzmann study. Physical Review E—Statistical, Nonlinear, and Soft Matter Physics 74.

(Continued)

*Primary Examiner* — Michael L Hobbs
(74) *Attorney, Agent, or Firm* — McDonnell Boehnen Hulbert & Berghoff LLP

(57) ABSTRACT

A soil-emulating device and a system for evaluation of soil-related properties are provided. The soil-emulating apparatus includes one or more soil micromodels comprising packed emulated soil particles. The packed soil particles comprise a particle size distribution, and a soil structure of a desired soil type. The soil micromodel is cast from a two-dimensional representation of a region to provide visualization of air infiltration into pores of the micromodel. The soil micromodel is located within an environmental control chamber to control humidity and, optionally, the soil micromodel is saturated with a bacteria strain. Images are captured of the soil micromodel over time.

16 Claims, 10 Drawing Sheets

(56) References Cited

OTHER PUBLICATIONS

Chau, J.F., Or, D., Sukop, M.G., 2005. Simulation of gaseous diffusion in partially saturated porous media under variable gravity with lattice Boltzmann methods. Water Resources Research 41, 1-11.

Chenu, C., 1993. Clay- or sand-polysaccharide associations as models for the interface between micro-organisms and soil: water related properties and microstructure. Geoderma 56, 143-156.

Cho, G.-C., Dodds, J., Santamaria, J.C., 2006. Particle shape effects on packing density, stiffness, and strength: natural and crushed sands. Journal of Geotechnical and Geoenvironmental Engineering 132, 591-602.

Cho, H.J., Jonsson, H., Campbell, K., Melke, P., Williams, J.W., Jedynak, B., Stevens, A.M., Groisman, A., Levchenko, A., 2007. Self-organization in high-density bacterial colonies: Efficient crowd control. Plos Biology 5, 2614-2623.

Deng, J., Dhummakupt, A., Samson, P.C., Wikswo, J.P., Shor, L.M., 2013. Dynamic dosing assay relating real-time respiration responses of *Staphylococcus aureus* biofilms to changing microchemical conditions. Analytical Chemistry 85, 5411-5419.

Emerson, W.W., McGarry, D., 2003. Organic carbon and soil porosity. Australian Journal of Soil Research 41, 107-118.

Flemming, H.-C., 2011. The perfect slime. Colloids and Surfaces B: Biointerfaces 86, 251-259.

Friedman, S.P., Robinson, D.A., 2002. Particle shape characterization using angle of repose measurements for predicting the effective permittivity and electrical conductivity of saturated granular media. Water Resources Research 38, 1236.

Gage, D.J., 2004. Infection and invasion of roots by symbiotic, nitrogen-fixing rhizobia during nodulation of temperate legumes. Microbiology and Molecular Biology Reviews 68, 280-300.

Galibert, F., Finan, T.M., Long, S.R., Puhler, A., Abola, P., al., e., 2001. The composite genome of the legume symbiont Sinorhizobium meliloti. Science 293, 668-672.

Jia, X., Williams, R.A., 2001. A packing algorithm for particles of arbitrary shapes. Powder Technology 120, 175-186.

Kim, H.J., Boedicker, J.Q., Choi, J.W., Ismagilov, R.F., 2008. Defined spatial structure stabilizes a synthetic multispecies bacterial community. Proceedings of the National Academy of Sciences 105, 18188-18193.

Langelier, S.M., Livak-Dahl, E., Manzo, A.J., Johnson, B.N., Walter, N.G., Burns, M.A., 2011. Flexible casting of modular self-aligning microfluidic assembly blocks. Lab Chip 11, 1679-1687.

Lanning L.M. Ford, R.M. Long, T., 2008. Bacterial chemotaxis transverse to axial flow in a microfluidic channel. Biotechnology and bioengineering 100, 653-663.

Long, T. Ford, R.M., 2009. Enhanced transverse migration of bacteria by chemotaxis in a porous T-sensor. Environmental science & technology 43, 1546-1552.

Mao, H., Cremer, P.S., Manson, M.D., 2003. A sensitive, versatile microfluidic assay for bacterial chemotaxis. Proceedings of the National Academy of Sciences 100, 5449-5454.

Markov, D.A., Samson, P.C., Schaffer, D.K., Dhummakupt, A., Wikswo, J.P., Shor, L.M., 2010. Window on a Microworld: Simple Microfluidic Systems for Studying Microbial Transport in Porous Media. Journal of Visualized Experiments 39.

Mueller, K., Gonzalez, J.E., 2011. Complex Regulation of Symbiotic Functions is Coordinated by MucR and Quorum Sensing in Sinorhizobium meliloti. Journal of Bacteriology 193, 485-496.

Mukhopadhyay, R., 2007. When PDMS isn't the best. Analytical Chemistry 79, 3248-3253.

Or, D., Wraith, J.M., 2002. Soil water content and water potential relationships, In: Warrick, A. (Ed.), Soil Physics Companion. CRC Press, Boca Raton, pp. 49-84.

Orner, et al. Abstract for Dec. 2013 AGU Meeting "Pore-scale Effects of Soil Structure and Microbial EPS Production on Soil Water Retention."

Orner et al. presentation Dec. 2013 AGU Meeting "Pore-scale Effects of Soil Structure and Microbial EPS Production on Soil Water Retention."

Pellock, B.J., Teplitski, M., Boinay, R.P., Bauer, W.D., Walker, G.C., 2002. A LuxR homolog controls production of symbiotically active extracellular polysaccharide II by Sinorhizobium meliloti. Journal of Bacteriology 184, 5067-5076.

Potts, M., 1994. Desiccation tolerance of prokaryotes. Microbiological Reviews 58, 755-805.

Rinaudi, L.V., Gonzalez, J.E., 2009. The Low-Molecular-Weight Fraction of Exopolysaccharide II from Sinorhizobium meliloti is a Crucial Determinant of Biofilm Formation. Journal of Bacteriology 191, 7216-7224.

Roman, G.T., Culbertson, C.T., 2006. Surface Engineering of Poly(dimethylsiloxane) Microfluidic Devices Using Transition Metal Sol-Gel Chemistry. Langmuir 22, 4445-4451.

Schindelin, J., Arganda-Carreras, I., Frise, E., Kaynig, V., Longair, M., Pietzsch, T., Preibisch, S., Rueden, C., Saalfeld, S., Schmid, B., Tinevez, J.Y., White, D.J., Hartenstein, V., Eliceiri, K., Tomancak, P., Cardona, A., 2012. Fiji: An open-source platform for biological-image analysis. Nature Methods 9, 676-682.

Scholl, M.A., Mills, A.L., Herman, J.S., Hornberger, G.M., 1990. The influence of mineralogy and solution chemistry on the attachment of bacteria to representative aquifer materials. Journal of Contaminant Hydrology 4, 321-326.

Schulte, E.E., and Hopkins, B.G, 1996. Estimation of soil organic matter by weight loss-on-ignition. Soil Science Society of America 46, 21-31.

Shor, Leslie M et al., Synergistic Effects of Soil Microstructure and Bacterial EPS on Drying Rate in Emulated Soil Micromodels, Soil Biology & Biochemistry 83 (2015) pp. 116-124.

Singh, R., Olson, M.S., 2011. Transverse mixing enhancement due to bacterial random motility in porous microfluidic devices. Environmental science & technology 45, 8780-8787.

Steinhaus, B., Garcia, M.L., Shen, A.Q., Angenent, L.T., 2007. A portable anaerobic microbioreactor reveals optimum growth conditions for the methanogen Methanosaeta concilii. Appl Environ Microbiol 73, 1653-1658.

Sukop, M.C., Or, D., 2003. Invasion percolation of single component, multiphase fluids with lattice Boltzmann models. Physica B 338, 298-303.

Wang, W., Shor, L.M., LeBoeuf, E.J., Wikswo, J.P., Kosson, D.S. 2005. Mobility of protozoa through narrow channels. Applied and Environmental Microbiology 71(8), 4628-4637.

Wang, W., Shor, L.M., LeBoeuF, E.J., Wikswo, J.P., Taghon, G.L., Kosson, D.S., 2008. Protozoa Migration in Bent Microfluidic Channels. Appl. Envir. Microbiol. 74, 1945-1949.

Weibel, D.B., DiLuzio, W.R., Whitesides, G.M., 2007. Microfabrication meets microbiology. Nature Reviews Microbiology 5, 209-218.

Whitesides, G., Ostuni, E., Takayama, S., Jiang, X., Ingber, D., 2001. Soft lithography in biology and biochemistry. Annual Review of Biomedical Engineering 3, 335-373.

\* cited by examiner

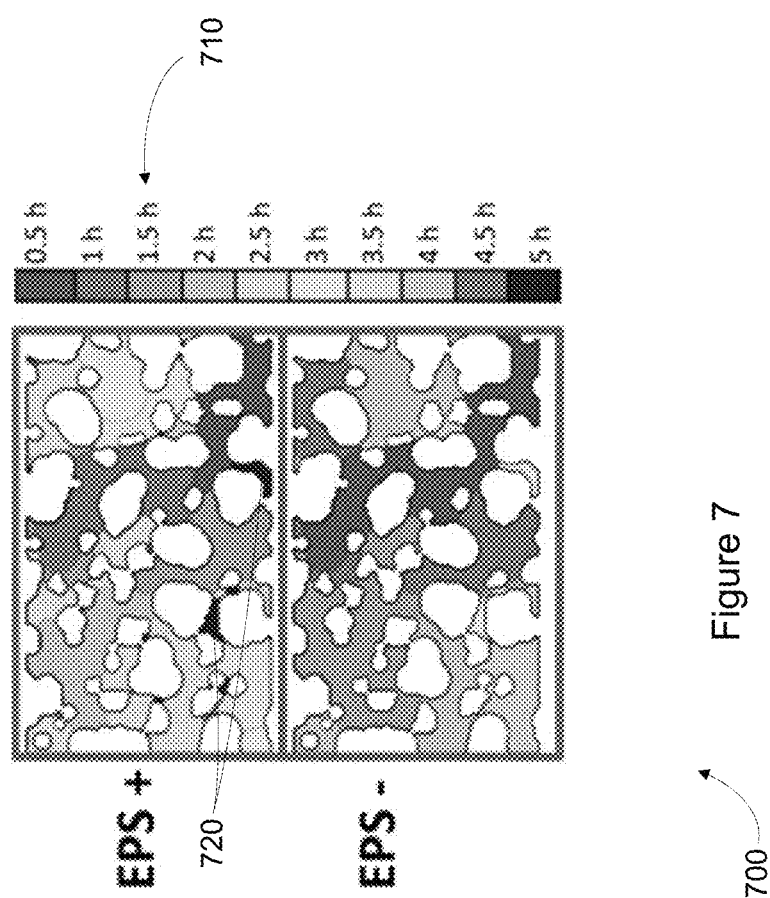

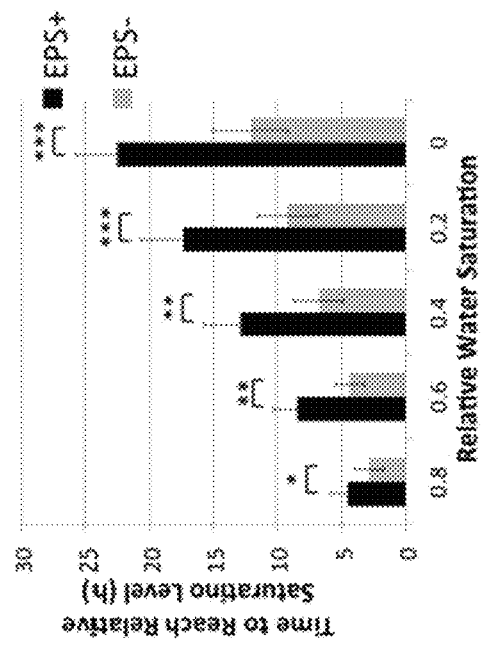
Figure 9
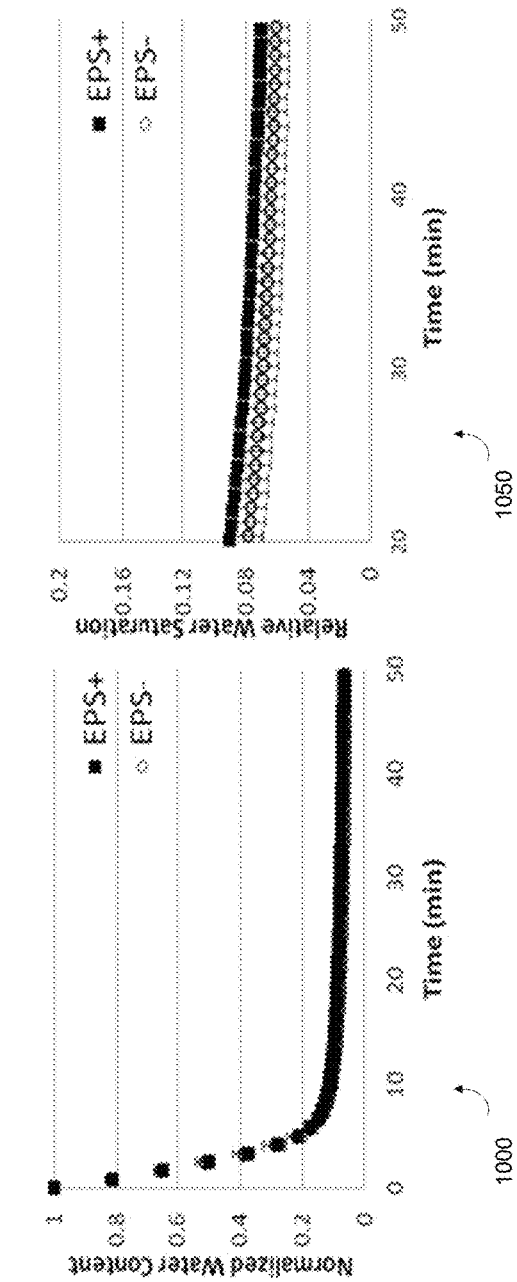
Figure 10a
Figure 10b

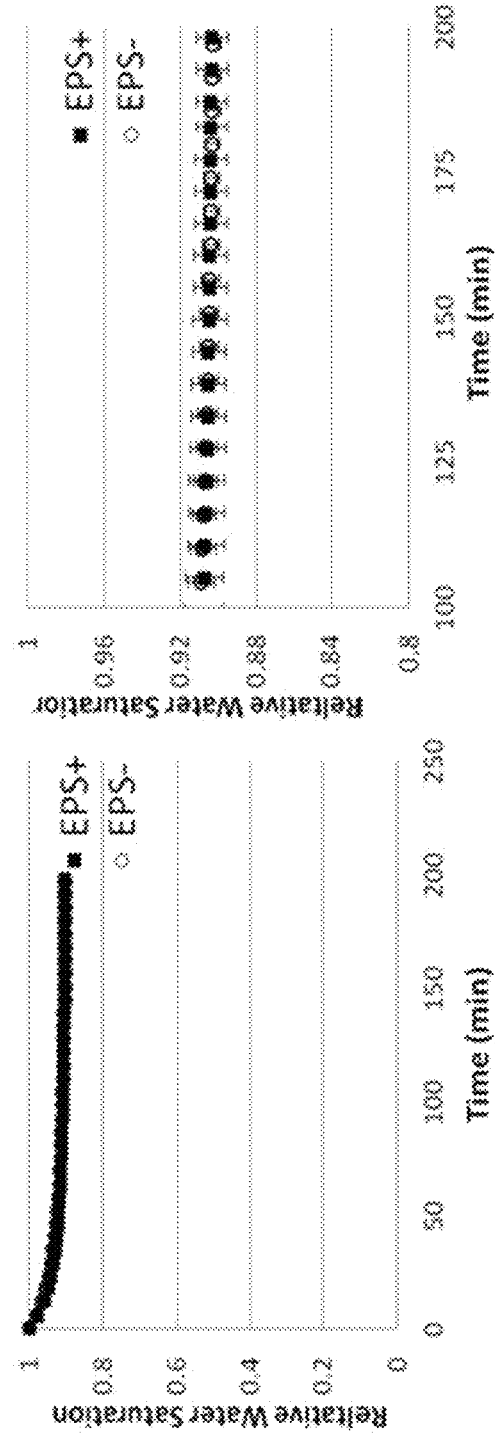

METHODS AND SYSTEMS TO REPLICATE SOIL PROPERTIES

CROSS-REFERENCE TO RELATED APPLICATIONS

This application claims priority to U.S. Provisional Patent Application Ser. No. 62/086,485 filed on Dec. 2, 2014, which is hereby incorporated by reference in its entirety.

STATEMENT REGARDING FEDERALLY SPONSORED RESEARCH OR DEVELOPMENT

This invention was made with government support under Grant No. 2012-67020-19380 awarded by the United States Department of Agriculture-National Institute of Food and Agriculture (USDA-NIFA). The government has certain rights in the invention.

BACKGROUND

Naturally occurring soils retain moisture under a range of climatic conditions, including dry conditions. The ability to retain moisture is an important factor in a soil's ability to support plants and other organisms present in a given ecosystem. A soil's ability to retain moisture is influenced by many factors, including its texture, structure, and the presence of active populations of soil microbes.

Soil moisture is an important factor influencing microbial respiration, and in turn, microbial processes modulate water availability in soil through production of extracellular polymeric substances (EPS). EPS is a hydrogel composed of deoxyribonucleic acid (DNA), protein, and polysaccharides that is naturally produced and secreted by many types of bacteria to form biofilms. EPS protects bacteria from predation, moderates nutrient availability, retains moisture in the colony, and promotes an aggregated soil structure.

Global climate change is predicted to amplify extreme events in a hydrological cycle, including powerful storms and prolonged droughts. Such extreme events can lead to widespread reduction in soil moisture, having implications for sustainable food, feed, and fiber production. One of the major factors limiting primary productivity in terrestrial ecosystems will be sub-optimal soil moisture.

A better understanding of the interaction between physical soil structure and biological processes is useful to predict the moderating effects of soil bacteria on retaining soil moisture, and may enable agriculture biotechnology that enhances natural soil processes for improved resiliency of terrestrial ecosystems.

SUMMARY

In accordance with the present invention, an apparatus, a system, and a method are defined for determining soil properties. In one embodiment, a soil-emulating apparatus comprises at least one soil micromodel region comprising packed emulated soil particles, the packed emulated soil particles comprising a particle size distribution and a soil structure of a desired soil type. The soil micromodel is cast from a two-dimensional representation of the region to provide visualization of air infiltration into pores of the soil micromodel.

In one example embodiment, the soil micromodel is positioned within a channel and is saturated with either a mucoid extracellular polymeric substance (EPS+) bacteria strain that produces well-characterized EPS, or a non-mucoid extracellular polymeric substance (EPS−) bacteria strain that does not produce any EPS. The soil micromodel comprises a biocompatible polymer, and may have at least one access port, as well as air infiltration openings to increase the sensitivity of measurements of water loss.

In another example embodiment, a system for evaluation of soil-related properties is provided, and comprises an environmental control chamber, at least one soil micromodel within the environmental control chamber, and a microscope. The at least one soil micromodel is cast from a two-dimensional representation of a region of packed emulated soil particles comprising a physical structure and a pore geometry of a desired soil type.

The environmental control chamber controls the humidity, and can provide a constant humidity.

The microscope is an inverted microscope.

In some embodiments, an imaging device for capturing images of the soil micromodel over time may be provided.

In another example embodiment, a method for determining soil properties is provided. The method includes providing a soil micromodel of packed emulated soil particles comprising particle sizes, a particle distribution, and a porosity of a desired soil type, saturating the soil micromodel with a bacteria, and imaging air infiltration into the soil micromodel over time.

Saturating the soil micromodel with a bacteria may comprise colonizing the soil micromodel with an EPS+ bacteria strain or an EPS− bacteria strain. The method may then further include determining from the imaging an effect of the EPS+ bacteria strain or the EPS− bacteria strain on changing water content of the soil micromodel.

In some embodiments, the method further comprises analyzing changing water content within the soil micromodel using thermal gravimetric analysis (TGA).

In some embodiments, the method further comprises imaging air infiltration at a pore scale as water evaporates from the soil micromodel. The method may be used to observe the effects of physical, chemical, or biological factors on pore-scale water retention. For example, the method may be used to measure drying resistance at a pore scale and to measure drying resistance as a function of bacterial EPS.

In another example embodiment, a method for preparing a soil micromodel is provided. The method comprises generating a three-dimensional region comprising a plurality of emulated soil particles, obtaining a two-dimensional representation of the region having a desired porosity and pore geometry, and casting a soil micromodel based on the two-dimensional representation.

These as well as other aspects and advantages of the synergy achieved by combining the various aspects of this technology, that while not previously disclosed, will become apparent to those of ordinary skill in the art by reading the following detailed description, with reference where appropriate to the accompanying drawings.

BRIEF DESCRIPTION OF THE FIGURES

FIG. 7 is a chromatic illustration of air infiltration over time for both EPS+ treatment and EPS− treatment, in accordance with at least one embodiment;

FIG. 9 depicts a graph plotting time to reach relative saturation level over relative water saturation, in accordance with at least one embodiment;

FIG. 10a depicts a graph plotting normalized water content over time, in accordance with at least one embodiment;

FIG. 10b depicts a graph plotting relative water saturation over time, in accordance with at least one embodiment;

FIG. 11a depicts a graph plotting relative water saturation over time, in accordance with at least one embodiment; and FIG. 11b depicts a graph showing a detailed view of the graph of FIG. 11a for the 100-200 minute time domain, in accordance with at least one embodiment.

DETAILED DESCRIPTION

In the following detailed description, reference is made to the accompanying figures, which form a part thereof. In the figures, similar symbols typically identify similar components, unless context dictates otherwise. The illustrative embodiments described in the detailed description, figures, and claims are not meant to be limiting.

Other embodiments may be utilized, and other changes may be made, without departing from the spirit or scope of the subject matter presented herein. It will be readily understood that the aspects of the present disclosure, as generally described herein, and illustrated in the figures, can be arranged, substituted, combined, separated, and designed in a wide variety of different configurations, all of which are explicitly contemplated herein.

I. Overview

EPS may allow plants to remain hydrated even with longer rain return intervals. The nitrogen-fixing bacteria *Sinorhizobium meliloti* is commonly found in soils and naturally produces EPS. Two mutant forms of *Sinorhizobium meliloti*, Rm 8530 EPS+ (EPS+), which over-expresses genes responsible for EPS production, and Rm 11609 EPS− (EPS−), the deletion of which causes no production of EPS, were used in the examples discussed herein.

In the exemplary devices, systems, and methods described herein, emulated soil micromodules were colonized with either EPS+ or EPS− bacteria strains, and air infiltration into the micromodels was imaged over time in a constant-humidity chamber placed on an inverted microscope.

Figure 1:
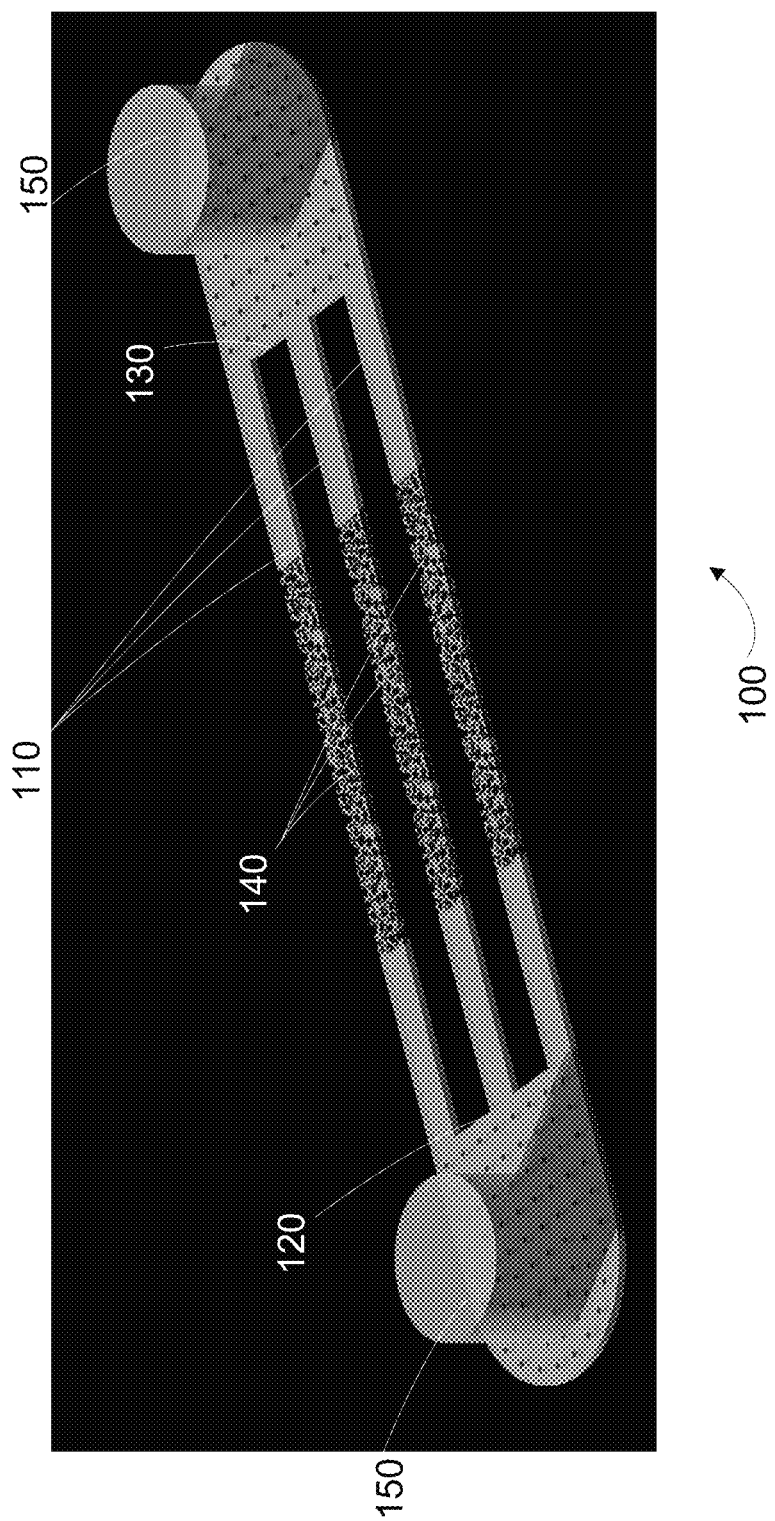
FIG. 1 depicts a schematic of an exemplary soil micromodel device in accordance with at least one embodiment.

FIG. 1 depicts a schematic of an exemplary soil micromodel device 100 in accordance with at least one embodiment. The device 100 may be used, among other things, to determine soil properties.

As shown in FIG. 1, the soil micromodel device 100 includes three channels 110 connected to an inlet wall 120 and an outlet wall 130, and at least one access port 150.

In one example embodiment, each channel 110 may comprise a 1 mm×20 mm×0.034 mm rectangle, and may contain a microstructured region 140 comprising a soil micromodel. In one example embodiment, the microstructured region 140 is 10 mm long. The microstructured region 140 is constructed from a computer-generated three-dimensional packing of ellipsoidal particles into a region. In one example embodiment, the region comprises a computational domain size of 100×100×100 voxels. The distribution of the packed ellipsoidal particles may be based on a desired soil type. For example, the distribution of the packed ellipsoidal particles may be based on a truncated, experimentally-determined sandy loam particle size distribution. In some example embodiments, particle diameters may range from 10-300 µm with an average diameter of 110 µm, and pore radii may range from 16 to 130 µm with an average hydraulic radius of 44 µm. Average particle diameters and pore radii (calculated as the hydraulic radius=2×area/perimeter) may be obtained by subjecting the original bitmap version of the soil micromodel to image analysis. Particle sizes in the soil fraction used for TGA ranged from 75-250 µm (obtained by sieving the whole soil). Typical porosities for a sandy loam are in the range of 25-35%.

From the three-dimensional region, a two-dimensional representation or slice may be selected and then converted to a two-toned bitmap. In one example embodiment, a program such as AutoCAD® may be used to manually outline and vectorize the particle contours in the bitmap prior to casting (described in further detail below). The resulting soil micromodel may then be partitioned to completely fill the microstructured region 140.

Figure 2:
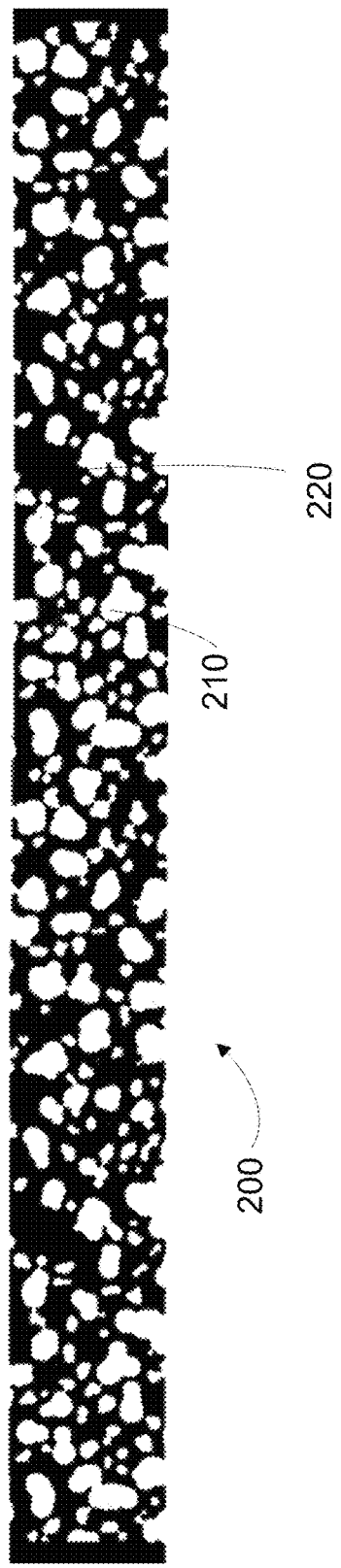
FIG. 2 depicts a tiled micrograph of two-dimensional pore structures that may be used in a soil micromodel, such as the soil micromodel of FIG. 1, in accordance with at least one embodiment.

FIG. 2 depicts a tiled micrograph of two-dimensional pore structures 210 and pore spaces 220 that may be used in a soil micromodel, such as the soil micromodel of FIG. 1, in accordance with at least one embodiment.

A soil micromodel may then be cast in a biocompatible polymer and set in one of the channels 110. In one example embodiment, the soil micromodel is cast in polydimethylsiloxane (PDMS) from a microfluidic casting master. Emulated soil micromodels may be cast 1 cm thick in PDMS, for example.

Microfluidic casting masters were created using photolithography. Finished masters may be silanized to facilitate repeated PMDS casting. To evenly oxidize the surface, the master may be treated with $O_2$ plasma. The casting is then aligned and bonded to a plasma-treated glass microscope slide in a configuration as depicted in FIGS. 3 and 4.

Figure 3:
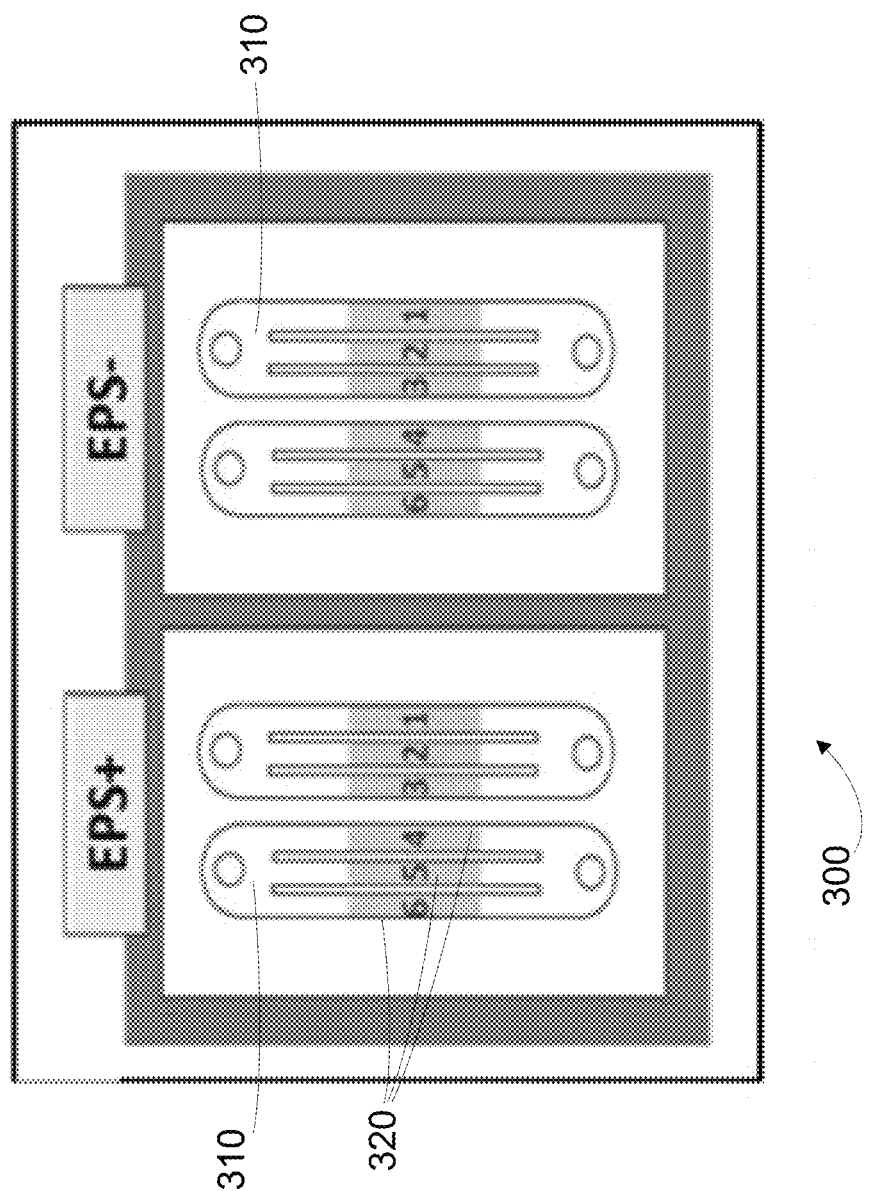
FIG. 3 depicts a schematic of an exemplary configuration of soil micromodels for a drying experiment, in accordance with at least one embodiment.

FIG. 3 depicts a schematic of an exemplary configuration 300 of soil micromodel devices 310 for a drying experiment, in accordance with at least one embodiment. The soil micromodel devices 310 are shown as each having three identical micro-structured drying channels 320. The soil micromodel devices 310 may be the same or similar to the soil micromodel device 100 of FIG. 1. As shown in FIG. 3, some of the soil micromodel devices 310 may be designated to be saturated with EPS+, while other soil micromodel devices 310 may be designated to be saturated with EPS−.

Figure 4:
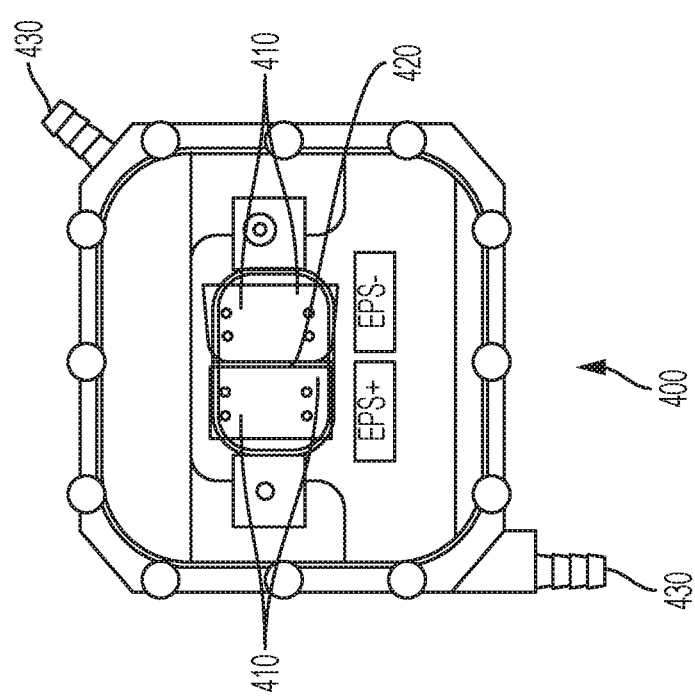
FIG. 4 depicts an exemplary environmental control chamber comprising soil micromodel devices and a viewing window, in accordance with at least one embodiment.

FIG. 4 depicts an exemplary environmental control chamber 400 comprising soil micromodel devices 410 and a viewing window 420, in accordance with at least one embodiment. The soil micromodel devices 410 may be installed within the environmental control chamber 400 in a configuration that is the same as or similar to that depicted in FIG. 3, for example. The micromodel devices 410 may be bonded or otherwise attached to the viewing window 420 of the environmental control chamber 400.

The viewing window 420 may comprise a clear or substantially transparent glass or plastic surface, allowing for viewing through the window.

The environmental control chamber 400 further comprises tube fittings 430 at two corners to allow humidity-controlled air to continuously circulate through the environmental control chamber 400. In one example embodiment, humidified air is created in a separate mixing chamber.

Once the micromodel devices 410 are attached to the viewing window 420, the micromodel devices 410 may be filled with suspensions of bacteria. The term filled may be used to mean that the micromodels are approximately 100% saturated.

The suspension of bacteria may comprise a suspension of EPS+ or EPS− bacteria in artificial groundwater, in some example embodiments. In one example embodiment, each bacterial strain is cultured for 5 days at 30° C. and 100 rpm in covered 20 ml rimless culture tubes in a medium also containing 0.4% glycerol, 500 μg ml$^{-1}$ streptomycin, and 100 μg/ml spectomycin. For the bacteria strain S. meliloti Rm 11609, the medium may also contain 100 μg ml$^{-1}$ neomycin and 0.75 μg ml$^{-1}$ oxytetracycline. Stationary phase cultures may be washed multiple times in artificial groundwater containing 0.100 mM $KH_2PO_4$, then adjusted to $OD_{595}$ 0.012 for S. meliloti Rm 8530 or $OD_{595}$ 0.010 for S. meliloti Rm 11609 to obtain comparable cell concentrations of $1\times10^7$ cells ml$^{-1}$.

II. Examples

In a recent study, soil micromodels were developed to better understand the pore-scale effects of bacterial EPS on drying resistance. The visualization and measurement of the effects of bacterial EPS at the pore scale is the physical scale most relevant to bacterial colonization and water retention processes. The study is discussed in Shor, Leslie M et al., *Synergistic Effects of Soil Microstructure and Bacterial EPS on Drying Rate in Emulated Soil Micromodels*, Soil Biology & Biochemistry 83 (2015) pages 116-124, which is incorporated herein by reference in its entirety.

Soil micromodel devices were prepared as discussed with reference to FIGS. 1-4, and were placed in an environmental control chamber in a configuration as depicted and discussed with reference to FIGS. 3-4.

Four replicate micromodels were filled with artificial groundwater (AGW) suspensions of bacteria: two with S. meliloti Rm 8530 (EPS+) and two with S. meliloiti Rm 11609 (EPS−), and were prepared according to the description with reference to FIG. 4. Then, all micromodels were held for a 5 day conditioning period at ambient temperature (about 23° C.) and about 100% relative humidity. This conditioning period allowed the bacterial community to stabilize biomass, aggregation state, and EPS production rate, and also allowed the PDMS polymer to saturate with water.

An HT10 USB Humidity Temperature Data Logger placed in the environmental control chamber continuously recorded humidity (78%±2%) and temperature (19° C.±0.5° C.) during the experiment. All soil micromodels were subject to identical, constant relative humidity and temperature boundary conditions, thus determining the potential of the water vapor according to $R_H = \exp((MW_w \psi_w)/(\pi_w RT))$, where $MW_w$ is the molecular weight of water, $\psi_w$ is water potential, $\pi_w$ is water density, R is the universal gas constant, and T is absolute temperature. The 80% relative humidity applied external to the soil micromodel corresponds to −30 MPa, representing extremely dry conditions under which bacterial respiration would cease in a real soil. This condition was chosen to produce reasonable drying times for both the real soil and the micromodels under EPS+ and EPS− conditions.

The progression of the air-water interface was determined throughout all of the microstructured regions within the twelve channels every 30 minutes from the time when the air interface was at the edge of the microstructured region until air had fully infiltrated. Bright-field composite images were captured using a Carl Zeiss® AxioObserver Z1 AX10 automated inverted microscope equipped with an AxioCam MRmRev 0.3 camera using a 5× objective using the Multidimensional Acquisition Module. Composite images were then constructed by stitching together nine overlapping frames using the AxioVision 4.8 software.

Figure 5:
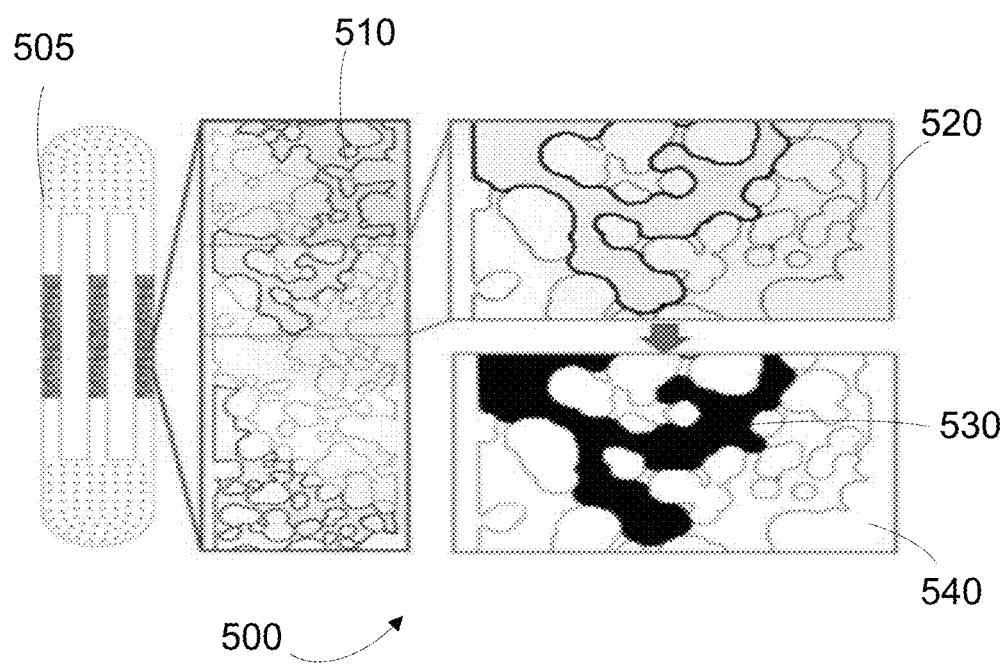
FIG. 5 depicts an example series of composite images, in accordance with at least one embodiment.

FIG. 5 depicts an example series 500 of composite images, in accordance with at least one embodiment. To analyze the composite images from a soil micromodel device 505, each composite image 510 was cropped and converted to a binary black and white image 520. Using a single threshold value, a continuous air interface along hydrated pore space or PDMS pillars could be resolved in all composite images. Next, the continuous air phase was manually filled with black pixels 530 using the position of the air interface as a guide, resulting in an image 540. The total pixels 530 at each time point in each composite image were quantified and then converted to an air volume using a uniform channel height of 34 μm. Finally, the air volume was subtracted from the known total pore volume to determine the remaining water volume or the relative water saturation.

As a qualitative support of the results obtained using soil micromodels, evaporation kinetics of a sandy loam soil amended with EPS+ or EPS− bacterial suspensions were measured using TGA. TGA involves gravimetric determination of water lost from a sample as a result of a predetermined temperature cycle. Bacterial-amended soils were first subjected to a period of desiccation and rewetting prior to TGA in order to better simulate the variable environmental conditions to which soil microbes are acclimated.

Paxton and Montauk fine sandy loam was collected from the Horsebarn Hill area of the University of Connecticut Storrs campus. Whole soil was screened in the field, autoclaved, air dried, and sieved to obtain the 75-250 μm fraction, corresponding to the particle size distribution of the soil micromodel. Excess volumes (5 ml) of bacterial AGW suspensions were added to 1 g sterile, air-dry soil in 50 ml centrifuge tube, then slurries were covered and allowed to sit at ambient temperature (approximately 23° C.) for 5 days. Slurries were dried at 60° C. for 2 days, then 100+/−1 mg dry bacteria-amended soil was loaded onto a tared hanging weigh pan. Dry bacteria-amended soil was re-hydrated by adding 40 μL of AGW, and equilibrated at 23° C. at 100% relative humidity for 2 hours prior to re-drying.

Replicate samples of EPS+ or EPS− S. meliloti-amended soil samples were loaded onto a TGA, and the change in weight was determined with time, as heated dry air flowed past the sample. Samples were dried at 40° C. for 700 minutes to estimate labile water under environmental conditions, then were dried at 105° C. for 120 minutes to determine total water. Finally, samples were oxidized at 360° C. for 120 minutes to determine the total organic carbon content.

Dynamic Vapor Sorption (Q5000, TA Instruments®) was used to measure the kinetics of water loss (i.e., evaporation) in pure bacterial biofilms collected from confluent bacterial lawns grown on agar plates. Liquid-phase S. meliloti Rm 8530 (EPS+) and Rm 11609 (EPS−) cultures were prepared as described above. Then, 300 µl aliquots of stationary-phase culture were added to agar plates with 0.4% glycerol, spread by shaking with 3 mm sterile glass beads, then incubated at 30° C. for 3 days. Samples of bacteria biofilm (approximately 10 mg) were scraped from the plates and placed into tared metalized quartz sample pans.

Because initial water content in agar plate scrapings may vary between replicates due to different ambient humidity and temperature on the day of experiments, bacterial biofilm samples were first dried to a consistent, low water content at 40° C. and 10% relative humidity in $N_2$ for 9 hours. Then, the humidity was increased to 90% in 10 min, and held steady for 9 hours to allow bacterial EPS to rehydrate and swell with water vapor. Finally, the humidity was decreased from 90% to 80%, for comparison with micromodel experiments, and the evaporation rate of water was determined gravimetrically.

Figure 6:
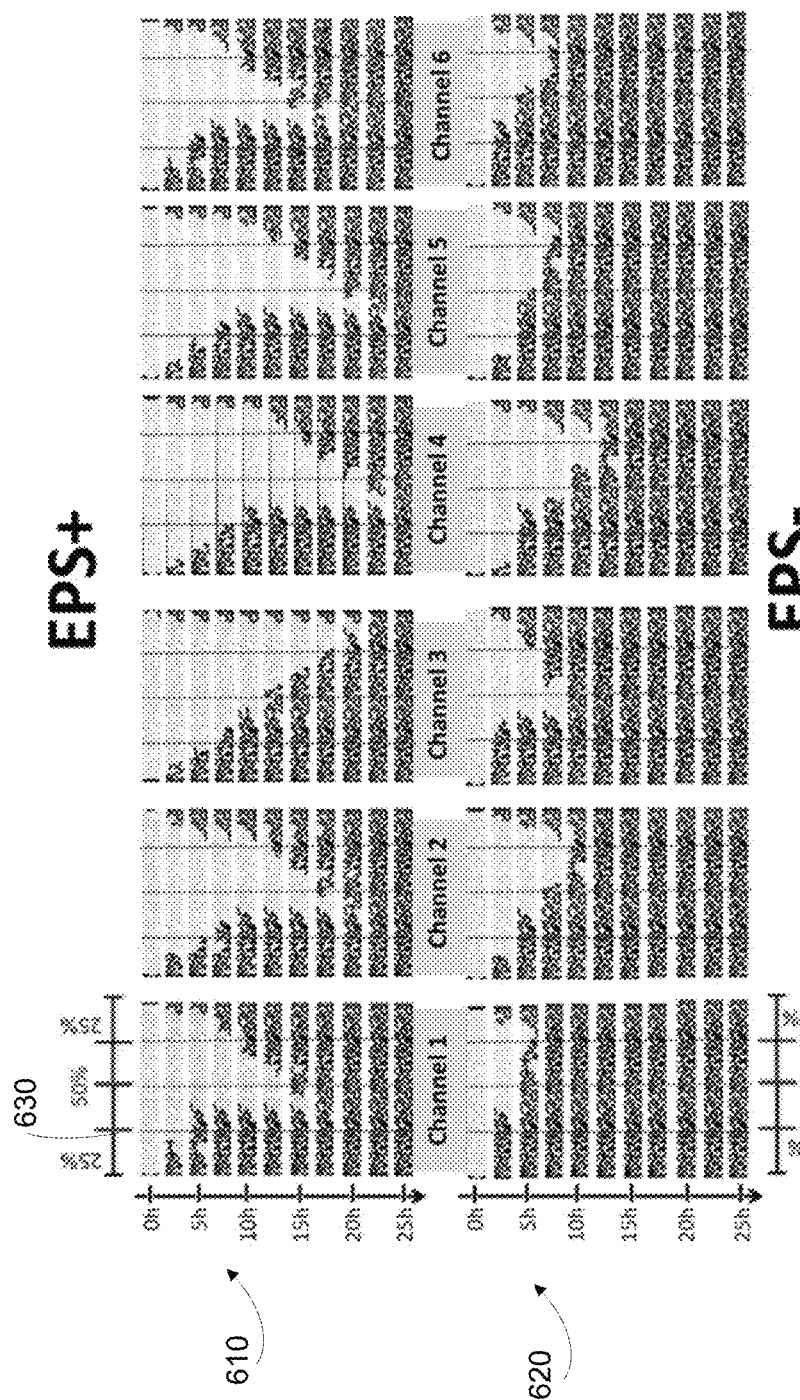
FIG. 6 depicts a time series of composite images showing air infiltration in replicate microstructures.

FIG. 6 depicts a time series of composite images 600 showing air infiltration in replicate microstructures. Channels filled with EPS+ are on the top row 610 and channels filled with EPS− are on the bottom row 620. The time lapse is plotted over the distances from each edge of a 20 mm long micro-structured region, expressed as a percentage. Vertical lines 630 signify the midline (50%) and the quartile (25%) distances from each edge of the micro-structured region.

Across treatments and replicates, microstructural features of the channel geometry constrained the progression of the air interface. For both EPS+ and EPS− treatments, air was observed to initially infiltrate more readily from the left side of each channel due to the random arrangement of pore throat sizes at the channel edges. Pore throat geometry also determined the advancement of the air-infiltration front, but the rate of advancement was different for EPS+ and EPS− replicates. In all replicates of both treatments, the air interface at the right remained fixed in either of two positions over several hours. For example, in channel 2 of the EPS− treatment, the air interface in the second composite image (after 2.5 hours of drying) was located about 8% across the channel, or about 1.6 mm from the right side, with similar results for channels 3-5. In the EPS+ treatment, the air interface also stalled at a similar position in channels 1, 3, 4, 5, and 6. However, the interface remained in this position much longer in the EPS+ treatments, up to 16.5 hours. A second stall position can be seen in several channels, for example, for channel 2 of the EPS+ treatment. This second stall position was also observed in the other five channels of the EPS+ treatment, but for shorter durations (typically 0.5 hours). This second stall position was apparent in all of the channels of the EPS− treatment for durations ranging from 2-5 hours.

Pore-scale patterns of air infiltration led to the persistence of hydrated pockets in large open pore spaces connected to the rest of the pore network by narrow pore throats similar across several of the channels. One such region that was visible across several of the channels can be visualized in channel 1 of the EPS− treatment, about 33% along the channel from the right side. This hydrated pocket persists longer in the EPS+ treatment than in the EPS− treatment. For example, it is observed in channel 1 and channel 6 of the EPS+ treatment for 5 frames each (at about 2 hours). The pocket is also observed in channels 1, 2, 4, and 5 of the EPS− treatment, but only for an average of 1 hour. Small hydrated pockets are also apparent in interstitial spaces between particles.

FIG. 7 is a chromatic illustration 700 of air infiltration over time for both EPS+ treatment and EPS− treatment, in accordance with at least one embodiment. The chromatic time scale 710 maps the persistence of hydration within a channel. In the EPS+ treatment, small spaces 720 measuring just a few microns remain hydrated for up to 5 hours. These same positions remained hydrated for 3 hours in the EPS− treatment.

Figures 8A, 8B:
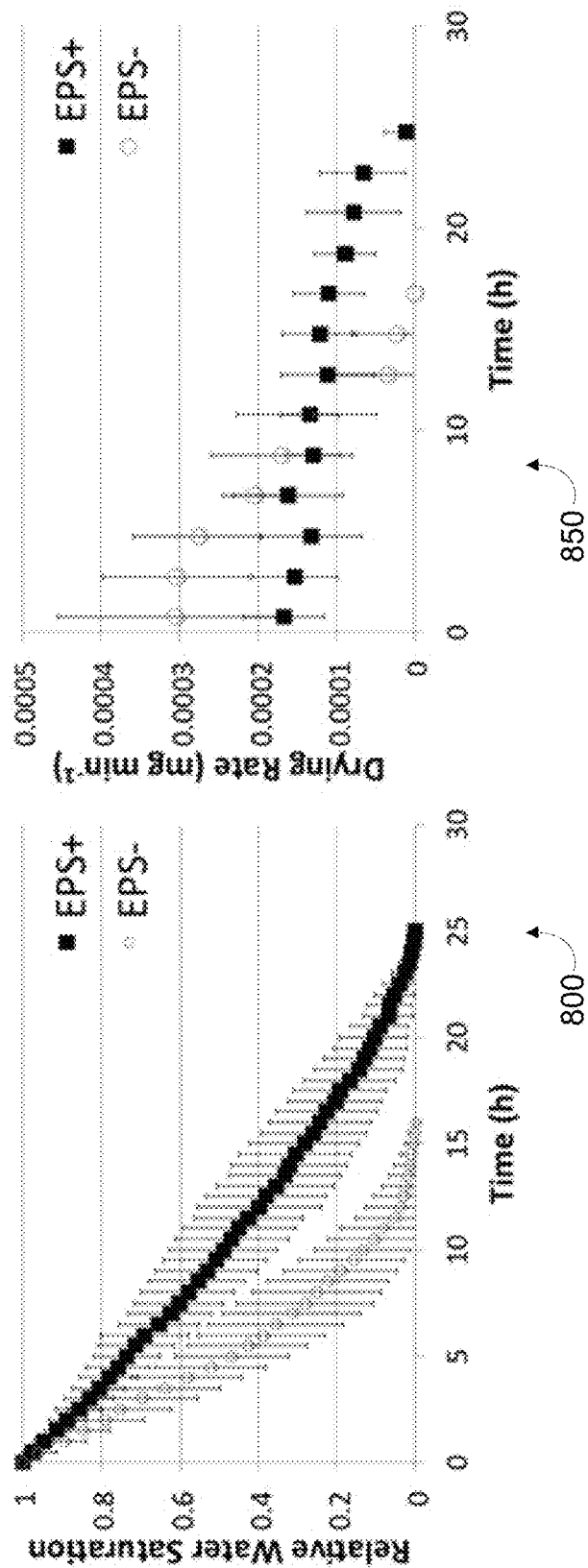
FIG. 8a depicts a graph plotting relative water saturation over time, in accordance with at least one embodiment.
FIG. 8b depicts a graph plotting drying rate over time, in accordance with at least one embodiment.

FIG. 8a depicts a graph 800 plotting relative water saturation over time, in accordance with at least one embodiment. Soil micromodels loaded with EPS+ suspensions retained moisture longer than micromodels loaded with EPS− suspensions. On average, EPS− dried in 12.1 hours with a standard deviation of 2.9 hours, and EPS+ dried in 22.7 hours with a standard deviation of 3.1 hours.

FIG. 8b depicts a graph 850 plotting drying rate over time, in accordance with at least one embodiment. The drying rate for channels filled with the EPS− suspension decreased continuously, from around 0.3 µg min$^{-1}$ at the beginning of the experiment to 0 within 20 hours. The drying rate for channels in the EPS+ treatment was more consistent over time: generally water was lost at a rate of 0.15 µg min$^{-1}$ for the first several hours and about 0.1 µg min$^{-1}$ from 5-10 hours.

At 11 hours into the drying process, average drying rates measured for the two treatments were similar (0.16 µg min$^{-1}$). At 11 hours, channels filled with the EPS− suspension were just 10% saturated, while channels filled with the EPS+ suspension were about 45% saturated. Towards the end of the drying process, the drying rate was greater in the EPS+ treatment channels (which still had much more water to lose) than the nearly-desiccated channels of the EPS− treatment.

FIG. 9 depicts a graph 900 plotting time to reach relative saturation level over relative water saturation, in accordance with at least one embodiment. Channels filled with EPS+ bacterial suspensions required more time to dry to a given relative saturation compared with channels filled with EPS− bacterial suspensions. EPS+ treatment channels required 4.5 hours±1.4 hours to reach 80% saturation versus 2.8 hours±1.1 hours for EPS− treatment channels. The EPS− treatment channels dried to 80% saturation 1.6× faster than the EPS+ treatment channels. Similarly, the time required to reach other milestones of 60%, 40%, 20%, and 0% relative water saturation were significantly shorter for EPS-treatment channels. The ratio of drying time in EPS− to EPS+ treatments for these milestones was a factor of 2.0, 1.9, 1.9, and 1.9 times faster, respectively.

The process of labile water loss from rewetted bacteria-amended soil was determined in duplicate for each bacterial strain treatment. FIG. 10a depicts a graph 1000 plotting normalized water content over time, in accordance with at least one embodiment. Water evaporation with moderate drying (40° C.) was normalized to the last 3 mg of water added into the 100 mg of soil.

FIG. 10b depicts a graph 1050 plotting relative water saturation over time, in accordance with at least one embodiment. As shown in FIG. 10b, no obvious difference in drying rate was observed between EPS− amended soil and EPS+ amended soil samples in the early stages of drying. However, from 20 to 50 minutes of drying of the last 3 mg water, the normalized water content was constantly lower in EPS− amended soil than that of EPS+ amended soil (p<0.0001). We believe that, although not as obvious as in the micromodels, this is evidence that EPS+ amended soil retains more water and can qualitatively support the micromodel results.

In the micromodels, the only openings for air infiltration are the ends of each of the channels. Air has to infiltrate from a 1 mm×34 μm opening into the channel and penetrate 5 mm along the channel from each end in 80% humidity, whereas in TGA experiments, bacteria amended soil was surrounded by air in a 0% humidity chamber. The much smaller air-water interface in the emulated soil structure and the higher humidity (80% vs. 0%) lead to increased sensitivity and exaggeratedly slow water loss dynamics in the micromodels.

Bacterial EPS can retain moisture in soil two ways: by holding water directly in the cross-linked hydrogel polymer itself, and through soil structuring which alters the physical arrangement of soil grains. To understand the ability of EPS to hold water directly without a physical structure, the swelling and drying behavior of duplicate biofilm samples collected from agar plates for both model strains were analyzed using dynamic vapor sorption.

The weight of each biofilm sample was normalized to its weight at equilibrium in 90% relative humidity. Then, once humidity was reduced to 80%, the loss of weight with evaporation was measured over time, as shown in FIG. 11a, depicting a graph 1100 plotting relative water saturation over time. FIG. 11b depicts a graph 1150 showing a detailed view of the graph 1100 for the 100-200 minute time domain. As shown in FIGS. 11a and 11b, there was no significant difference in water content in pure bacterial biofilms from the EPS+ and EPS– strains.

The physical geometry of the micromodels determines the path taken by the invading air phase. Air invasion into a porous medium exhibits invasion-percolation behavior in which the non-wetting fluid (i.e., air) first invades the largest pore throat where capillary forces are weakest. Once the throat is breached, the comparatively large pore space behind it fills with air quickly (i.e., the water evaporates), followed by the next-largest pore throat of the new interfacial configuration.

Here, air infiltration behavior is consistent with invasion-percolation behavior. The path taken by the air interface was observed to follow similar patterns across treatments and replicates. Certain regions in the channels readily admitted the invading air space, while other regions with narrow pore throats were associated with stall positions of the air interface, or boundaries of persistent hydrated pockets. As in natural porous media, water is held more strongly in narrow hydrophilic spaces between PDMS pillars where capillarity is strongest.

Apart from slight lithography or casting flaws, the physical geometry for this study was conserved across replicate channels and in each micromodel casting. Microfabrication thus conserves the physical geometry across treatments and replicates, resulting in reproducible patterns of air infiltration. However, live bacteria move, grow, and respire within the channels. The resulting spatial distribution and population density of microbial communities and the chemical composition of the interstitial fluid after the 5 days conditioning period may vary between replicates, and especially if bacteria have aggregated at critical pore throats. The variable behavior of the bacterial population may have been responsible for the variations observed in air infiltration across replicates.

The chemical composition of the interstitial fluid limits the rate of evaporation from channels. Here, fluid in the pore spaces contains a mixture of bacterial cells, salts, proteins, small molecules, and especially in the EPS+ treatment, an extracellular polymeric matrix. Hydrogels are known to retain moisture through the favorable entropy of mixing between $H_2O$ molecules and the EPS polysaccharide, resulting in a lower activity of water in the hydrogel phase relative to pure water phase.

Here it was shown, for both whole soils and soil micromodels, amendment with the EPS+ strain resulted in a marked evaporation resistance. The evaporation time was ranged from 1.1 to 2.5× slower in replicate micromodels, with an average of 1.9× slower for the EPS+ versus EPS– treatment. In whole soil, water content is higher when approaching dryness ($p<0.0001$). However, additional experiments are needed to test the applicability of the technique to other questions and other systems.

Surprisingly, no difference in water content was observed from pure biofilm collected from agar plates between EPS+ and EPS– strains of *S. meloliti*. The fact that evaporation resistance is only seen in a micro-structured matrix (soil or microdevice), and not in a pure biofilm sample suggests a synergistic effect of physical microstructure and chemical features of the biological sample in evaporation resistance.

This study demonstrates that microbes can modulate water availability at the pore scale. The average wilting point for many crops is between 15 and 27% soil moisture. Here, micromodels filled with the EPS– bacterial suspension dropped below 15% saturation at about 10 hours. Meanwhile, physically identical micromodels filled with the EPS+ bacterial suspension were still 50% saturated at 10 hours.

Modulating the rate of water loss may have stronger implications for agriculture than the absolute amount of water retained in a soil. Global circulation models do not necessarily predict changes in the amount of precipitation in many areas, but the rain that comes will be associated with more extreme events separated by longer rain return intervals. The result of changing precipitation patterns is a robust prediction of reduced soil moisture in many regions. Soil amendment with EPS-producing strains has the potential to slow evaporation. In combination with the effects of EPS on soil structure, the drying-resistance effects demonstrated here may translate to an important field-scale effect, active on longer timescales than those in the present study.

Although the study described herein employed a single physical pore geometry, the system and method are amenable to systematic alteration of physical pore geometry.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims, along with the full scope of equivalents to which such claims are entitled. It is also to be understood that the terminology used herein is for the purpose of describing particular embodiments only, and is not intended to be limiting.

What is claimed is:

1. A soil-emulating apparatus comprising:
   an inlet wall;
   an outlet wall;
   at least one access port fluidically connected to one or both of the inlet wall and the outlet wall;
   at least one channel extending between the inlet wall and the outlet wall;
   at least one soil micromodel region comprising emulated soil particles positioned within the at least one channel, wherein the emulated soil particles comprise particles having a diameter of between 10 μm and 300 μm.

2. The soil-emulating apparatus of claim 1, wherein the channel is saturated with an aqueous suspension of live bacteria.

3. The soil-emulating apparatus of claim 2, wherein the aqueous suspension includes one of the following: a mucoid extracellular polymeric substance (EPS+) bacteria strain, or a non-mucoid extracellular polymeric substance (EPS−) bacteria strain.

4. The soil-emulating apparatus of claim 1, wherein the emulated soil particles comprise a biocompatible polymer.

5. The soil-emulating apparatus of claim 1, further comprising:
   air infiltration openings through the at least one soil micromodel.

6. The soil-emulating apparatus of claim 1, further comprising:
   an environmental control chamber, wherein the at least one soil micromodel is positioned within a channel within the environmental control chamber; and
   a microscope.

7. The soil-emulating apparatus of claim 6, wherein the channel is saturated with a mucoid extracellular polymeric substance (EPS+) bacteria strain or a non-mucoid extracellular polymeric substance (EPS−) bacteria strain.

8. The soil-emulating apparatus of claim 6, wherein the environmental control chamber provides a constant humidity via circulation of humidity-controlled air.

9. The soil-emulating apparatus of claim 6, wherein the microscope is an inverted microscope.

10. The soil-emulating apparatus of claim 6, further comprising an imaging device for capturing images of the soil micromodel over time.

11. The soil-emulating apparatus of claim 1, wherein pores of the at least one soil micromodel have a radius of between 16 μm and 130 μm.

12. The soil-emulating apparatus of claim 2, wherein pores of the at least one soil micromodel have a radius of between 16 μm and 130 μm.

13. The soil-emulating apparatus of claim 4, wherein pores of the at least one soil micromodel have a radius of between 16 μm and 130 μm.

14. The soil-emulating apparatus of claim 1, wherein the emulated soil particles comprise ellipsoidal particles.

15. The soil-emulating apparatus of claim 12, wherein the emulated soil particles comprise ellipsoidal particles.

16. The soil-emulating apparatus of claim 13, wherein the emulated soil particles comprise ellipsoidal particles.

* * * * *